(12) United States Patent
Otsubo

(10) Patent No.: US 7,803,243 B2
(45) Date of Patent: *Sep. 28, 2010

(54) METHOD FOR MAKING DISPOSABLE PANTS-TYPE DIAPER

(75) Inventor: Toshifumi Otsubo, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 365 days.

This patent is subject to a terminal disclaimer.

(21) Appl. No.: 11/923,193

(22) Filed: Oct. 24, 2007

(65) Prior Publication Data

US 2008/0110553 A1    May 15, 2008

(30) Foreign Application Priority Data

Nov. 15, 2006  (JP) ............................. 2006-309653

(51) Int. Cl.
*A61F 13/15* (2006.01)

(52) U.S. Cl. .................... 156/226; 156/227; 156/292; 604/385.01

(58) Field of Classification Search .................... None
See application file for complete search history.

(56) References Cited

U.S. PATENT DOCUMENTS 3,926,189 A * 12/1975 Taylor ........................ 604/359
4,573,990 A    3/1986 Ohsaki
5,554,142 A * 9/1996 Dreier et al. ........... 604/385.23
6,409,711 B1 * 6/2002 Jonbrink ................. 604/385.01
6,508,798 B1    1/2003 Widlund et al.
6,648,868 B2 * 11/2003 Sayama et al. ......... 604/385.22
6,824,534 B2 * 11/2004 Mishima et al. ........ 604/385.01

FOREIGN PATENT DOCUMENTS

JP    2002-011044 A    1/2002

* cited by examiner

*Primary Examiner*—Richard Crispino
*Assistant Examiner*—Barbara J. Musser
(74) *Attorney, Agent, or Firm*—Lowe Hauptman Ham & Berner, LLP

(57) ABSTRACT

A disposable pants-type diaper includes a separator interposed between the inner surface of a pants-type skin-covering assembly and the wearer's skin so as to protect the wearer's skin from being soiled with feces. The separator comprises a separator extending from a bottom of a crotch region of the diaper toward a front waist region and a rear waist region and fixed to the crotch region along transversely opposite margins thereof. The separator has a front end and a rear end both extending in a transverse direction of the crotch region and elastically extensible and contractible. In a transversely middle of the crotch region, these front and rear end edges are spaced from the inner surface of the absorbent chassis and joined integrally with each other.

7 Claims, 12 Drawing Sheets

FIG.9
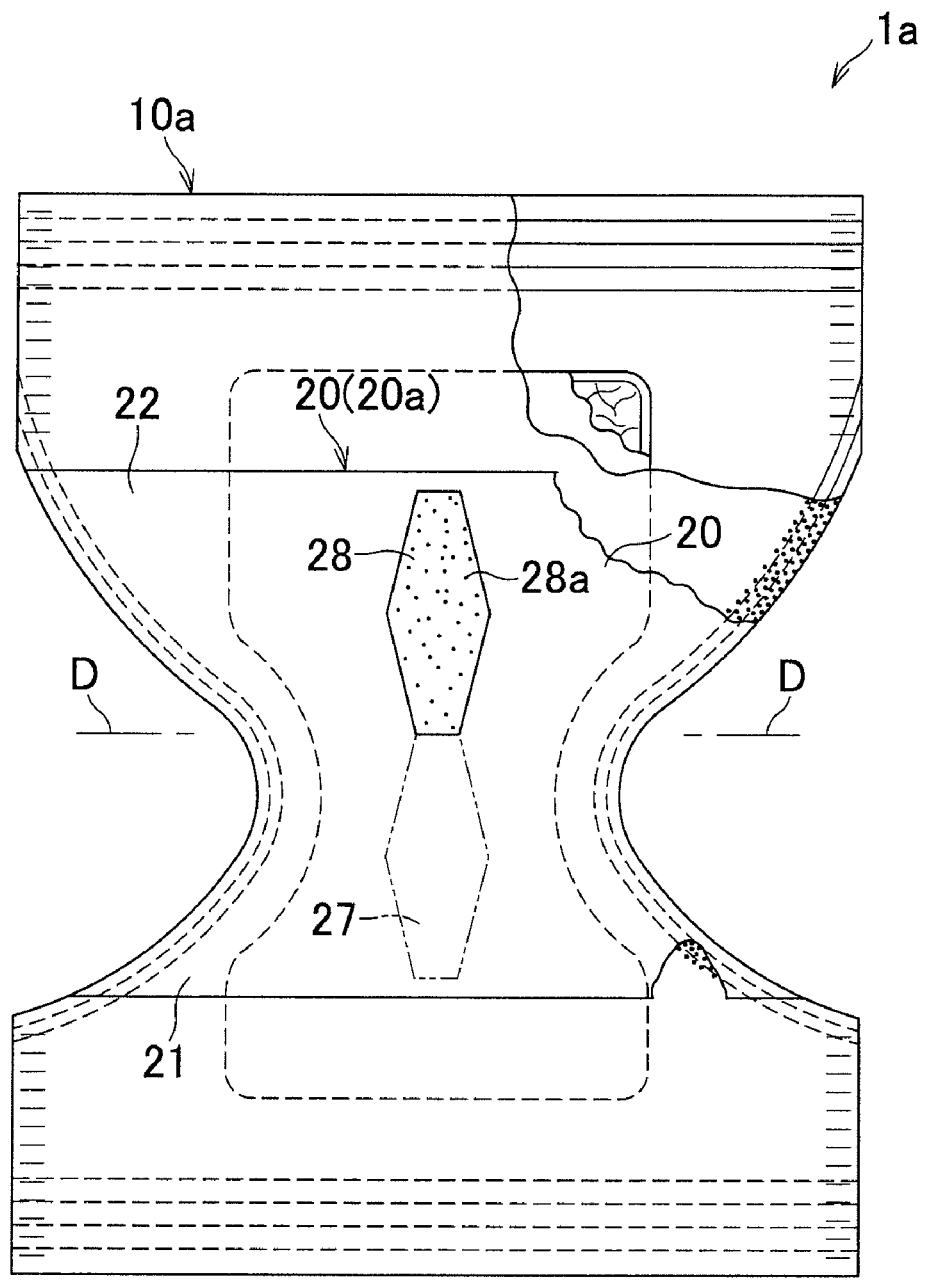
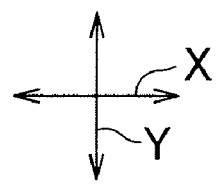

METHOD FOR MAKING DISPOSABLE PANTS-TYPE DIAPER

The entire discloses of Japanese Patent application No. 2006-309653 filed on Nov. 15, 2006 including specification, drawings and abstract are herein incorporated by reference in its entirety.

BACKGROUND OF THE INVENTION

The present invention relates to a method for making a disposable pants-type diaper and the pants-type diaper obtained by this method, and particularly to the method for making the pants-type diaper adapted to prevent feces from coming in contact with the wearer's skin and such pants-type diaper.

Disposable diapers adapted to prevent feces from coming in contact with and thereby soiling the wearer's skin is well known. For example, a pants-type diaper disclosed in Japanese Unexamined Patent Application Publication No. 2002-11044 (REFERENCE) has a skin contactable sheet provided on the topsheet and the crotch region of this skin contactable sheet is formed with an opening around which an elastic member is in its stretched state to the skin contactable sheet. The opening is exactly opposed to the wearer's anus so that feces discharged from the wearer may move through the opening into a space underlying the skin contactable sheet without an anxiety that feces might come in the wearer's skin.

The diaper disclosed in REFERENCE is not free from the possibility that feces might move into a space between the wearer's skin and the skin contactable sheet and significantly soil the wearer's skin unless the opening formed in the skin contactable sheet is exactly opposed to the wearer's anus. Specifically, it is essential for the diaper of prior art to bring the opening of the skin contactable sheet in line with the anus in the course of putting the diaper on the wearer's body. However, it can not be determined from the exterior whether the opening of the diaper having been put on the wearer's body is exactly opposed to the anus or not. Furthermore, the skin contactable sheet is formed with a notch through which urine can be directly absorbed by the absorbent material. However, urine which has passed through the notch will be inevitably mixed with feces on the surface of the absorbent material. Liquidity of feces will increase when it is mixed with urine and consequentially a possibility that the wearer's skin might be soiled with feces will correspondingly increase.

SUMMARY OF THE INVENTION

In view of the problem of the conventional diaper as has been described above, it is an object of the present invention to provide a novel disposable pants-type diaper facilitating the wearer's anus to oppose a feces receiving space exactly, thereby protecting the wearer's skin from being soiled with feces.

The object set forth above is achieved by first, second and third aspects of the present invention. Of these aspects, the first and second aspects aims to provide a method for making a disposable pants-type diaper basically comprising the steps of preparing a basic structure having a crotch region, a front waist region extending forward from the crotch region and a rear waist region extending rearward from the crotch region, bonding the front and rear waist regions to each other along transversely opposite margins of the front and rear waist regions to make the basic structure in pants-shape and providing the basic structure on its inner side facing the wearer's skin with s separator adapted to prevent feces from coming in contact with the wearer' skin.

The first aspect of the present invention comprises the steps of: preparing a separator extending on the inner side of the basic structure in a back-and-forth direction of the crotch region from a longitudinal middle of the crotch region into the front and rear waist regions, and extending in a transverse direction of the crotch region so as to straddle a longitudinal center line bisecting a transverse dimension of the crotch region; fixing transversely opposite margins of the separator extending in the back-and-forth direction to the inner side on both sides of the longitudinal center line, and spacing a region of the separator defined between the transversely opposite margins; folding back the basic structure in said back-and-forth direction along a transverse center line with the separator inside and then integrating a front end of the separator extending in parallel to the transverse center line with a rear end of the separator extending in parallel to the transverse center line on the longitudinal center line; and bonding transversely opposite margins of the front waist region to the transversely opposite margins of the rear waist region in the basic structure to form the separator from the separator.

According to one preferred embodiment of the first aspect, the front and rear end edges of the separator are integrated with each other in a joining region previously formed by bonding agent such as hot melt adhesive or pressure-sensitive adhesive.

According to another preferred embodiment of the first aspect, the joining region is formed by folding back a sheet-like joining member coated on its one surface with the bonding agent along a folding line extending in parallel to the transverse center line with the bonding agent outside and then bonding one of halves formed as a result of folding back to associated one of the front and rear end edges.

According to still another preferred embodiment of the first aspect, the front and rear end edges of the separator are integrated with each other by means of sonic or heat sealing technique.

According to yet another preferred embodiment of the first aspect, the method further includes a step of partially bonding the region of the separator defined between the transversely opposite margins to the basic structure in the vicinity of the transverse center line.

The second aspect of the present invention comprises steps of: preparing a first separator comprising a first half extending on the inner side of the basic structure so as to be put aside toward the front waist region from a transverse center line bisecting a dimension of the basic structure and a second half extending on the inner side of the basic structure so as to be put aside toward the rear waist region from the transverse center line, the first separator extending in the transverse direction of the crotch region so as to stride a longitudinal direction bisecting a transverse dimension of the crotch region; fixing transversely opposite margins of the first separator extending in the back-and-forth direction to the inner side on both sides of the longitudinal center line, and spacing a region of the first separator defined between the transversely opposite margins; placing a second separator not larger than one of the first and second halves upon the one of the first and second halves; bonding the one of the halves and the second separator to each other on the longitudinal center line while the one of the halves is left spaced from the second separator on both sides of the longitudinal center line; coating the second separator on its surface opposite to its surface bonded to the one of the halves with adhesive; folding back the basic structure along the transverse center line in the back-and-forth direction with the first separator inside; bonding the other of the halves to the opposite surface of the second separator by means of the adhesive; and bonding transversely opposite margins of the front waist region to the transversely opposite margins of the rear waist region in the basic structure to form the separator from the first separator.

According to one preferred embodiment of the second aspect, the first separator is fixed to the inner side of the basic structure after the second separator has previously been bonded to the one of the halves.

According to the third aspect of the present invention, the disposable pants-type diaper including the separator is obtained by the method according to any one of the first and second aspects of the present invention.

The method for making the disposable pants-type diaper according to the first aspect of the present invention comprises the steps of fixing the separator extending in the back-and-forth direction and in the transverse direction of the crotch region to the inner surface of the basic structure, folding back the basic structure along the transverse center line, bonding the front and rear waist regions of the basic structure thus folded back to each other along the transversely opposite margins thereof, and then the front and rear end edges of the separator are permanently integrated with each other on the longitudinal centerline of the basic structure. In this way, the basic structure takes the pants-shape. Thereupon, the pocket-like urine receiving space is formed between the front section of the crotch region in the basic structure and the separator while the pocket-like feces receiving space is formed between the rear section of the crotch region in the basic structure and the separator. In these bodily waste receiving spaces, the front and rear end edges of the separator integrated with each other on the longitudinal center line come in contact with the inner sides of the wearer' legs while the crotch region of the basic structure is spaced from these front and rear end edges. Consequentially, the respective pocket-like bodily waste receiving spaces are kept opened and reliably receive urine and feces, respectively, independently of the state in which the diaper is put on the wearer's body. In this way, the separator forming these bodily waste receiving spaces effectively function as the separator protecting the wearer's skin from contact with urine and feces.

According to the embodiment wherein one of the front and rear end edges of the separator is previously formed with the joining region, the basic structure may be merely folded back to permanently integrate the front and rear end edges of the separator with each other and thereby to facilitate formation of the separator and the bodily waist receiving spaces with this separator.

According to the embodiment wherein the joining member comprises the folded sheet-like joining member, the joining member may be dimensioned to be appropriately large in the transverse direction to ensure that the front and rear end edges of the separator forming the separator can be easily bonded to each other. In addition, the distance between the front and rear end edges of the separator at the joint region can be adjusted by appropriately adjusting the dimension of the joining member in the back-and-forth direction.

According to the embodiment wherein the front and rear end edges of the separator are integrated with each other by means of sonic or heat sealing technique, irritation of the wearer's skin due to the region of integration can be alleviated in comparison with the case in which the front and rear end edges are integrated with each other by means of adhesive.

According to the embodiment wherein the region of the separator defined between the transversely opposite margins thereof is bonded to the basic structure in the vicinity of the transverse center line, the bodily waste receiving space on the side of the front waist region and the bodily waste region on the side of the rear waist region are positively divided. Consequentially, urine and feces might not be possibly mixed with each other within the bodily waste receiving space.

With method according to the second aspect of the present invention, the one half of the first separator is bonded to the second separator and the other half is bonded to the second separator as the basic structure is folded back. Thereby the first half is integrated with the second half by means of the second separator. Therefore, the second separator may be dimensioned to be appropriately large to facilitate the first half to be integrated with the second half.

The effect provided by the pants-type diaper according to the third aspect of the present invention will be understood from the description given hereunder with reference to the accompanying drawings.

BRIEF DESCRIPTION OF THE DRAWINGS

FIG. 9 is a view similar to FIG. 2, showing still another preferred embodiment of the diaper as has been developed;

DETAILED DESCRIPTION OF THE PREFERRED EMBODIMENTS

Details of a method for making a disposable pants-type diaper according to the present invention will be more fully understood from the description made hereunder with reference to the accompanying drawings.

Figure 1:
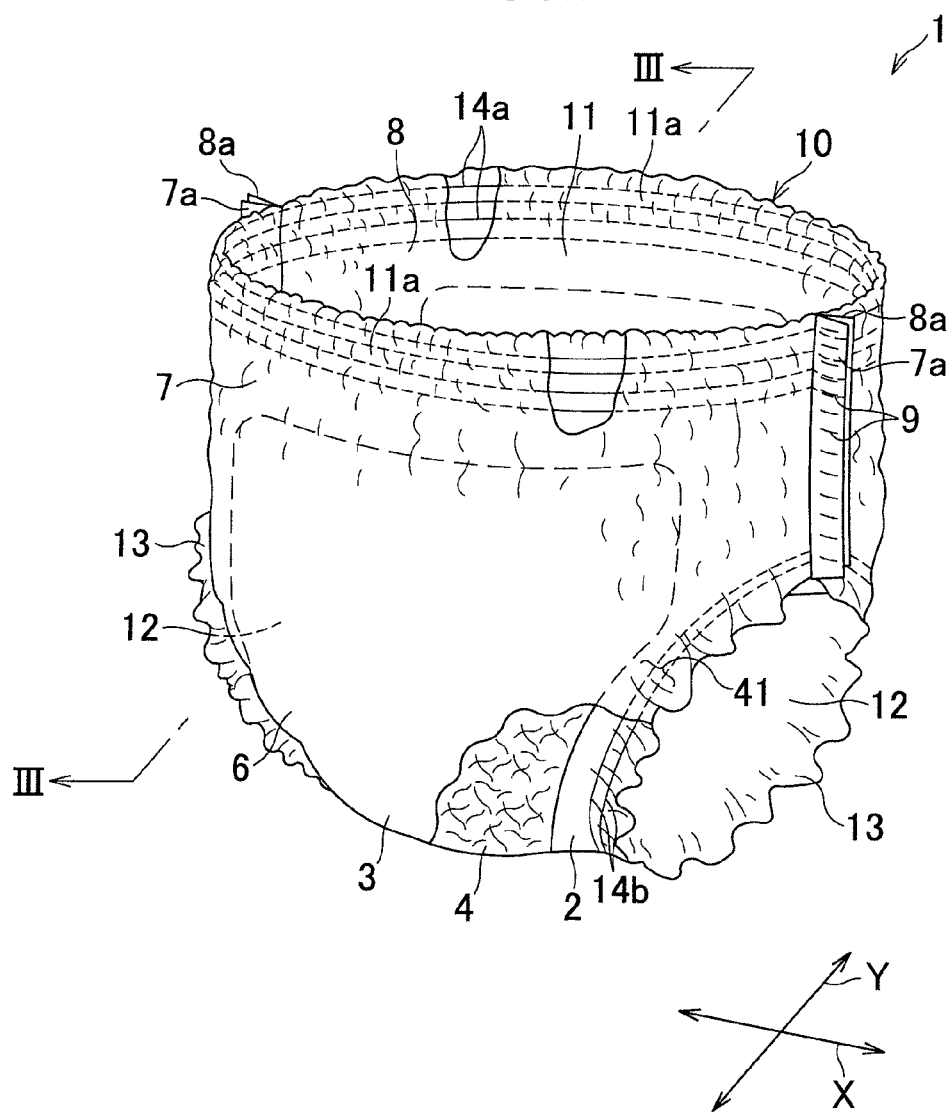
FIG. 1 is a partially cutaway perspective view of a pants-type diaper.

FIG. 1 is a partially cutaway perspective view showing a disposable pants-type diaper 1 obtained by a method according to the present invention for making the same as put on the wearer's body. The pants-type diaper 1 has a pants-type absorbent chassis 10 comprising a liquid-pervious bodyside liner 2, a liquid-impervious outside sheet 3 and a body fluid absorbent material 4 sandwiched between these two sheets 2, 3. The absorbent chassis 10 is configured to define a crotch region 6, a front waist region 7 extending forward from the crotch region 6 and a rear waist region 8 extending rearward from the crotch region 6. The front and rear waist regions 7, 8 are put flat together along respective lateral margins 7a, 8a of thereof and seamed together at a series of welding spots 9 arranged along these lateral margins intermittently in a vertical direction as viewed in FIG. 1 so as to form a waist-hole 11 and a pair of leg-holes 12. Sandwiched between the bodyside liner 2 and the outside sheet 3, waist elastic members 14a circumferentially extend along a periphery defining the waist-hole 11a and are secured in a stretched state to at least one of the bodyside liner 2 and the outside sheet 3. In a similar manner, leg elastic members 14b sandwiched between the bodyside liner 2 and the outside sheet 3 circumferentially extend along each periphery 13 defining each of the leg-holes 12 and are secured in a stretched state to at least one of the bodyside liner 2 and the outside sheet 3 so that these leg elastic members 14b, bodyside liner 2 and the outside sheet 3 may form annular elastic regions 41 around the respective legs.

Figure 2:
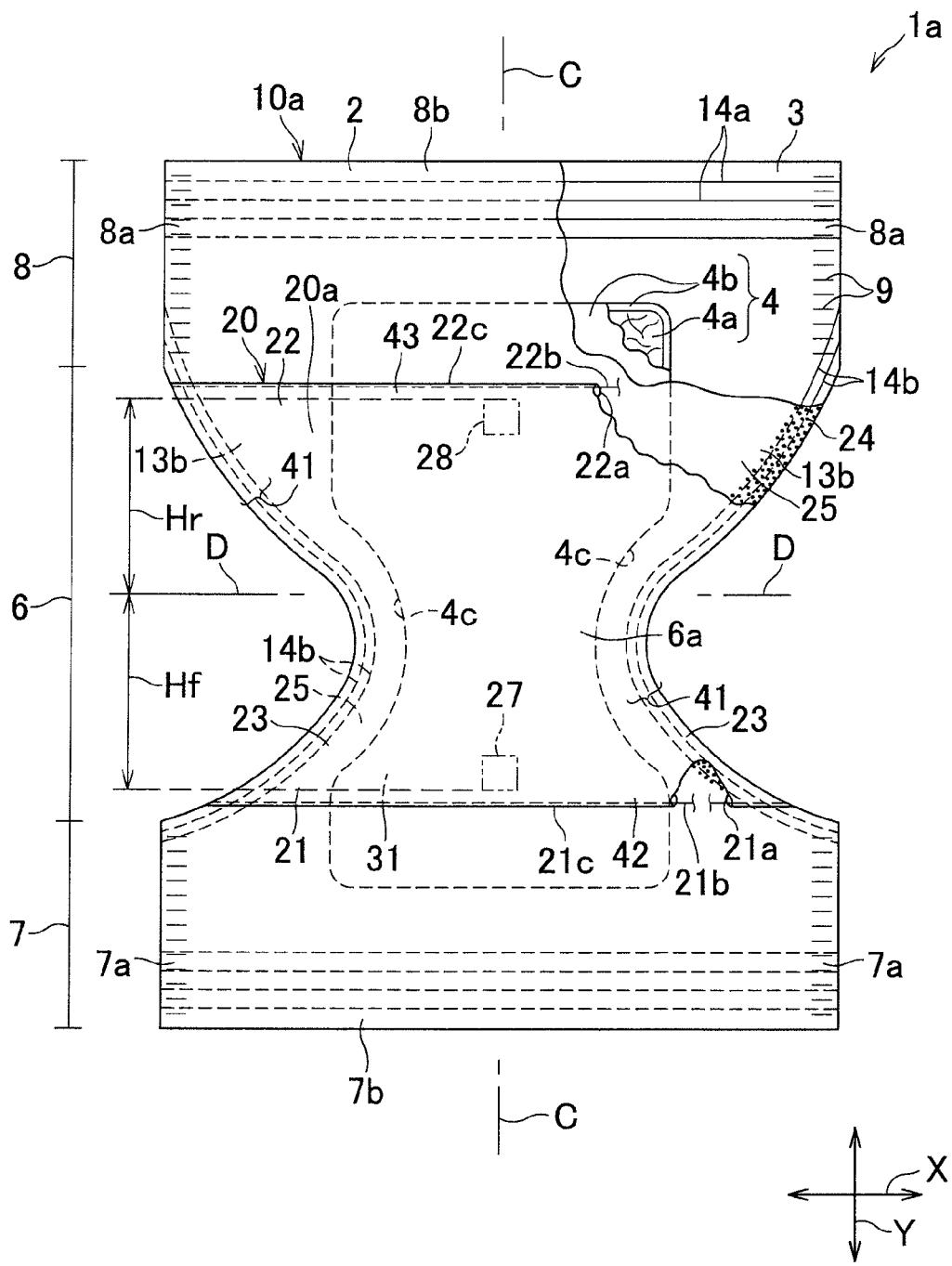
FIG. 2 a plan view showing the pants-type diaper having front and rear waist regions peeled from each other, developed and flattened.

FIG. 2 is a partially cutaway plan view showing a developed diaper 1a corresponding to the pants-type diaper 1 of FIG. 1 having the front and rear waist regions 7, 8 peeled off from each other at the welding spots 9 and then fully developed in a transverse direction indicated by the double-headed arrow X as well as in a back-and-forth direction indicated by a double-headed arrow Y which is orthogonal to the transverse direction. FIG. 2 shows an inner side, i.e., bodyside of such developed diaper 1a. In the developed diaper 1a, the pants-type absorbent chassis 10 corresponds to a generally hourglass-shaped basic structure 10a. The periphery 11a of the waist-hole 11 in FIG. 1 corresponds, in FIG. 2, to a front end 7b and a rear end 8b of the basic structure 10a while the peripheries 13 of the respective leg-holes 12 correspond, in FIG. 2, to transverse margins 13b of the crotch region of the basic structure 10a. While these lateral margins 13b curve toward a longitudinal center line C-C bisecting a width of the basic structure 10a, the lateral edges 7a, 8a of the front and rear waist regions 7, 8, respectively, extend in the back-and-forth direction Y substantially in parallel to the longitudinal center line C-C. The absorbent material 4 also is generally hourglass-shaped and comprises a mixture 4a of fluff pulp and super-absorbent polymer particles wrapped with a covering sheet 4b having a high absorbability as well as high spreadability for body fluids such as a tissue paper. In the basic structure 10a, the bodyside liner 2 defining the inner side thereof is provided with a separator 20 made of a hydrophobic sheet material, preferably made of a hydrophobic and liquid-impervious sheet material so as to serve as a separator 20a (See FIG. 3).

The separator 20 has lateral edges 23 fixed to the lateral edges 13b of the crotch region, respectively, by means of hot melt adhesive 24, a front end 21 lying in the crotch region 6 aside toward the front waist region 7 so as to extend in the transverse direction X to the respective lateral margins 13b of the crotch region 6 and a rear end 22 lying in the crotch region 6 aside toward the rear waist region 8 so as to extend in the transverse direction X to the respective lateral margins 13b of the crotch region 6. Except for the lateral edges 23, the separator 20 is substantially free from the bodyside liner 2 so that a tunnel- or pocket-like bodily waste receiving space 31 can be between the separator 20 and the bodyside liner 2. The front end 21 and the rear end 22 respectively have sleeves 21a, 22a formed by folding back the respective ends 21, 22 of the separator 20. These sleeves 21a, 22a respectively contain a front elastic member 21b and a rear elastic member 22b attached in a stretched state thereto to form a front elastic region 42 and a rear elastic region 43, respectively, extending between the lateral edges 13b of the crotch region 6. These elastic regions 42, 43 intersect with elastic regions 41 formed by the leg elastic members 14b, the bodyside liner 2 and the outside sheet 3 in the basic structure 10a. The front end 21 and the rear end 22 are substantially at equal distances from a transverse center line D-D and respectively include a front joint region 27 and a rear joint region 28 indicated by imaginary lines on the longitudinal center line C-C.

From the developed diaper 1a comprising the basic structure 10a provided with the separator 20 in the manner as has been described above, the pants-type diaper 1 is obtained by a method comprising the steps as will be described hereinafter. First, the front joint region 27 and/or the rear joint region 28 may be coated with bond such as hot melt adhesive or pressure-sensitive adhesive. Then the developed diaper 1a is folded back the bodyside liner 2 with the bodyside liner 2 inside along the transverse center line D-D. The front joint region 27 and the rear joint region 28 are exactly placed upon each other as the developed diaper 1a is folded back in this manner so that these front and rear joint regions 27, 28 may be joined together by means of the bond to form a joint region 35 (See FIG. 3) in the pants-type diaper 1. The lateral edges 7a of the front waist region 7 and the lateral edges 8a of the rear waist region 8 in the basic structure 10a are also exactly placed upon as the developed diaper 1a is folded back so that these lateral edges 7a, 8a, respectively, may be bonded together at the welding spots as shown in FIG. 1, for example, by means of so-called sonic sealing technique.

In the pants-type diaper 1 obtained in this manner, the basic structure 10a defines the pants-type absorbent chassis 10 and the separator 20 cooperates with the basic structure 10a to define the bodily waste receiving space 31 and at the same time to define the separator 20a (See FIG. 3) serving to prevent the wearer's skin from coming in contact with urine and feces. In the basic structure 10a of FIG. 2, the absorbent material 4 sandwiched between the bodyside liner 2 and the outside sheet 3 extends from a bottom 6a of the crotch region 6 in the back-and-forth direction Y preferably beyond the front end 21 and the rear end 22 of the separator 20 as seen in FIG. 2. However, it is not essential for the present invention relating to the method for making the pants-type diaper whether the basic structure 10a includes the absorbent material 4 or not and whether the absorbent material 4 is of a specific configuration or not.

Figure 3:
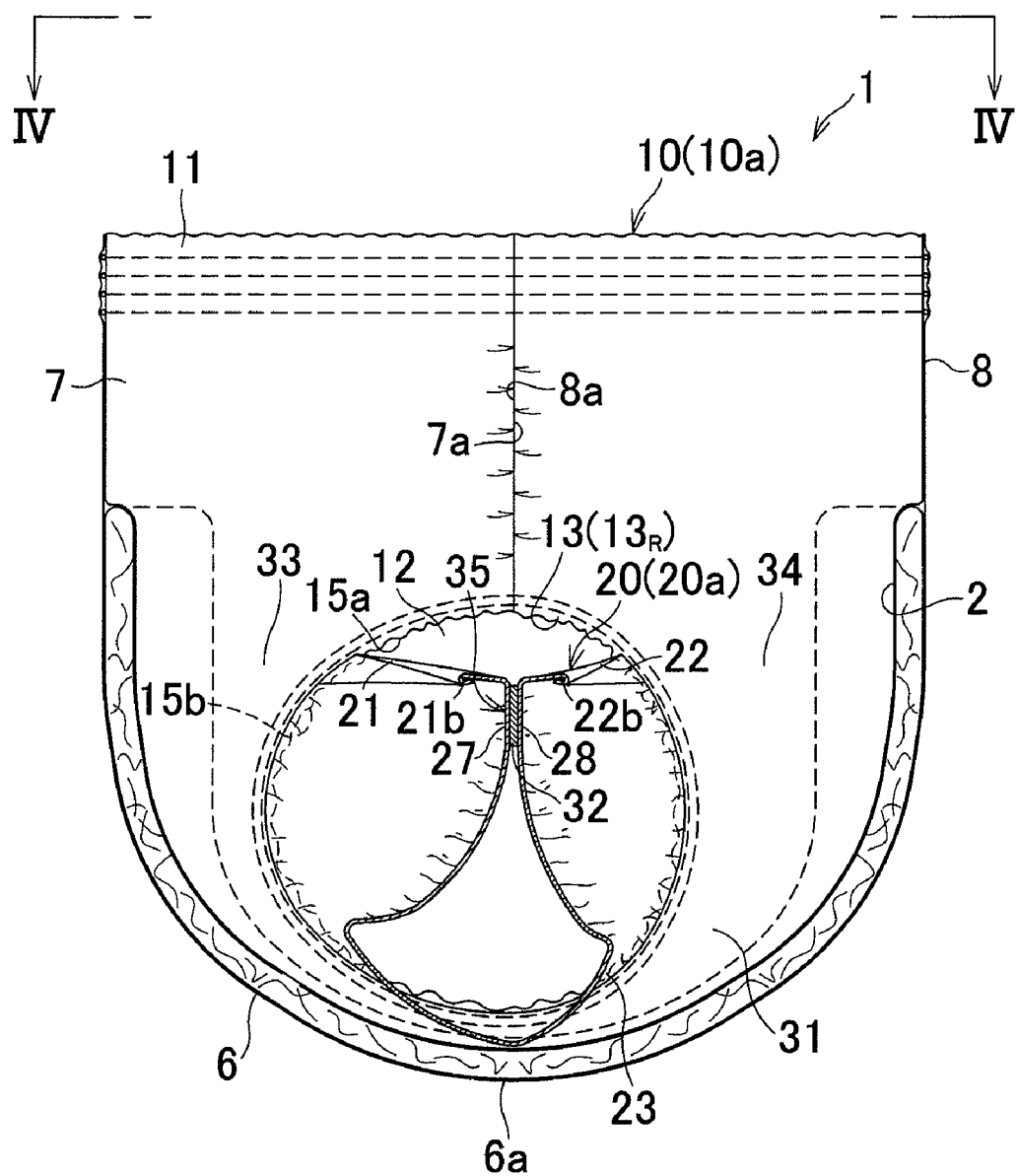
FIG. 3 is a sectional view taken along the line III-III in FIG. 1.

FIG. 3 is a sectional view taken along the line III-III in FIG. 1 wherein the line III-III conforms to the longitudinal center line C-C. The pants-type absorbent chassis 10 includes the front waist region 7 and the rear waist region 8 seamed together along the lateral edges 7a, 8a, respectively. The crotch region 6 shown in FIG. 2 now curves in FIG. 3 substantially in a U-shape and the lateral edges 13b of the crotch region 6 now appear as the peripheries 13 defining the respective leg-holes 12. The separator 20 appears in FIG. 3 as the separator 20a having the joint region 35 in which the front end 21 and the rear end 22 of the separator 20 are permanently bonded together by means of the bond 32 such as hot melt adhesive or pressure-sensitive adhesive. The bodily waste receiving space 31 defined by the separator 20a and the bodyside liner 2 of the basic structure 10a has a front opening 33 defined by the front end 21 together with the bodyside liner 2 and a rear opening 34 defined by the rear end 22 together with the bodyside liner 2. At the bottom 6a defined by the lowest portion of the crotch region 6, the bodyside liner 2 and the separator 20a are substantially or really in contact with each other.

Figure 4:
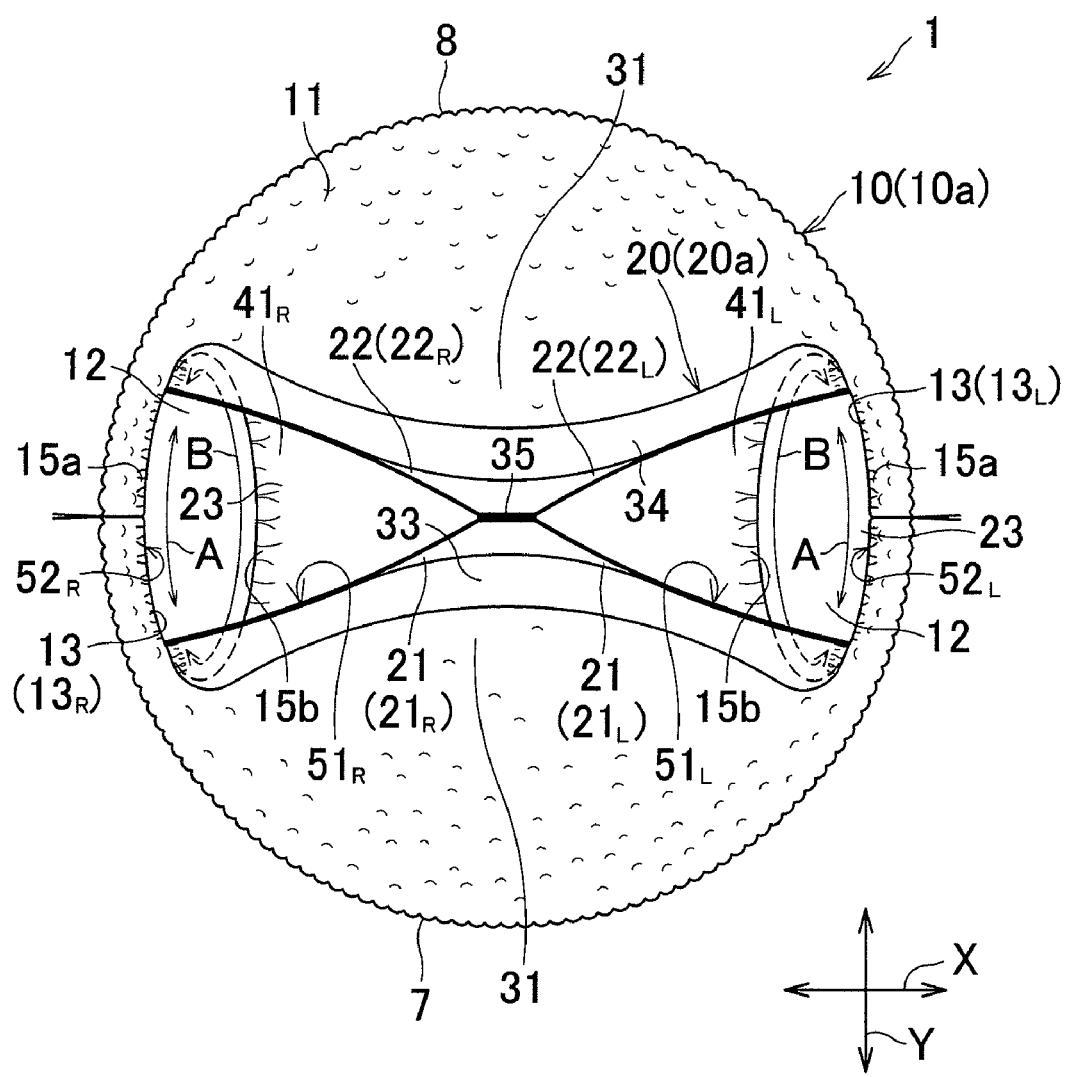
FIG. 4 is an overhead view of the pants-type diaper as viewed in a direction indicated by the arrow line IV-IV.

FIG. 4 is an overhead view of the diaper 1 as viewed in a direction indicated by the arrowed line IV-IV in FIG. 3, i.e., as viewed from above the waist-hole 11. The front end 21 of the separator 20a has its dimension in the transverse direction X bisected by the joint region 35 into a front end segment $21_R$ for the right leg and a front end segment $21_L$ for the left leg. The front end segment $21_R$ is adapted to be held in close contact with the right leg of the wearer and the front end segment $21_L$ is adapted to be held in close contact with the left leg of the wearer wherein these front end segments $21_R$, $21_L$ describe a V-shape in FIG. 4. The rear end 22 also has its dimension in the transverse direction X bisected by the joint region 35, in the same manner as the front end 21, into a rear end segment $22_R$ for the right leg and a rear end segment $22_L$ for the left leg. The rear end segment $22_R$ is adapted to be held in close contact with the right leg of the wearer and the rear end segment $22_L$ is adapted to be held in close contact with the left leg of the wearer wherein these rear end segments $21_R$, $21_L$ describe a V-shape in FIG. 4. The respective peripheries 13 of the leg-holes 12 in the absorbent chassis 10 comprise a periphery $13_R$ for the right leg and a periphery $13_L$ for the left leg wherein each of the peripheries $13_R$, $13_L$ is divided into an upper segment 15a left free from the associated lateral margin 23 of the separator 20a and a lower segment 15b joined to the associated lateral margin 23 of the separator 20a (See FIG. 3 also). In FIG. 4, a range in which the upper segment 15a extends and a range in which the lower segment 15b extends are represented by double-headed arrows A and B, respectively.

A sequence in which the pants-type diaper of such configuration is put on the wearer's body and how the pants-type diaper 1 behaves in the course of being put on the wearer's body will be described. First, the front and rear waist regions 7, 8 of the absorbent chassis 10 is spaced from each other in the back-and-forth direction Y and thereby the waist-hole 11 is broadened as seen in FIGS. 1 and 4. Thereupon, the front end segment $21_R$ for the right leg and the front end segment $21_L$ for the left leg constituting the front end 21 of the separator 20a are deformed about the joint region 35 so as to describe the V-shape and, in a similar way, the rear end segment $22_R$ for the right leg and the rear end segment $22_L$ for the left leg constituting the rear end 22 of the separator 20a are deformed so as to described the V-shape. Such deformation causes the front opening 33 and the rear opening 34 to be automatically broadened (See FIG. 3). At the same moment, the front end segment $21_R$ for the right leg and the rear end segment $22_R$ for the right leg are widely spaced from each other while the front end segment $21_L$ for the left leg and the rear end segment $22_L$ for the left leg are widely spaced from each other. Now the right leg of the wearer (not shown) is guided through an opening 41R for the right leg defined by the upper segment 15a of the periphery segment $13_R$ of the associated leg-hole 12, the front end segment $21_R$ for the right leg of the separator 20a and the rear end segment $22_R$ for the right leg of the separator 20a. The right leg is guided further through the right leg-hole 12 defined by the upper segment 15a and the lower segment 15b of the periphery segment $13_R$ for the right leg. Then the left leg is guided through an opening 41L for the left leg defined by the upper segment 15a of the periphery segment $13_L$ for the left leg, the front end segment $21_L$ for the left leg and the rear end segment $22_L$ for the left leg. The left leg is guided further through the left leg-hole 12 defined by the upper segment 15a and the lower segment 15b of the periphery segment $13_L$ for the left leg.

In the pants-type diaper 1 put on the wearer's body in the manner as has been described above, the peripheries 13 of the respective leg-holes 12, i.e., the periphery $13_R$ for the right leg and the periphery $13_L$ for the left leg are elastically extensible and contractible around the respective holes 12 while the front end 21 and the rear end 22 of the separator 20a are elastically extensible and contractible in the transverse direction X. In the vicinity of the right groin, therefore, the upper segment 15a of the periphery $13_R$ for the right leg, the front end segment $21_R$ for the right leg and the rear end segment $22_R$ for the right leg are elastically held in close contact around the right leg to form a primary seal $51_R$ (See FIG. 4) serving to prevent leak of body fluids from occurring around the right leg. Below the primary seal $51_R$, the lower segment 15b and the upper segment 15a of the periphery $13_R$ cooperate integrally with each other to form a secondary seal $52_R$ (See FIG. 4) serving to prevent leak of body fluids from occurring around the right leg. This secondary seal $52_R$ functions in a similar manner to the manner in which the leg-surrounding seal in the conventional pants-type diaper function. Just as the case of the right leg, in the vicinity of the left groin, therefore, the upper segment 15a of the periphery $13_L$ for the left leg, the front end segment $21_L$ for the left leg and the rear end segment $22_L$ for the left leg are elastically held in close contact around the left leg to form a primary seal $51_L$. Below the primary seal $51_L$, the lower segment 15b and the upper segment 15b of the periphery $13_L$ cooperate integrally with each other to form a secondary seal $52_L$. The pants-type diaper put on the wearer's body may be sufficiently pulled up along the waist to ensure that the front end 21 and the rear end 22 of the separator 20a, in the vicinity of the joint region 35, come in contact with a zone of the wearer's crotch region defined between the wearer's external genital and anus. Even after the pants-type diaper 1 has been put on the wearer's body, the front end 21 as well as the rear end 22 of the separator 20a is maintained spaced from the bodyside liner 2 and the front opening 33 as well as the rear opening is maintained widely broadened.

With the pants-type diaper 1 put on the wearer's body in this manner, the separator 20a distinctly separates the wearer's crotch region into a front half and a rear half so that the front opening 33 is reliably opposed to the wearer's external genital and the rear opening 34 is reliably opposed to the anus. It is ensured, therefore, that urine discharged from the external genital is guided through the front opening 33 into the pocket-like bodily waste receiving space 31 while feces discharged from the anus is guided through the rear opening 34 into the bodily waste receiving space 31. In this way, the separator 20a effectively prevents urine and/or feces from coming in contact with the wearer's skin. A possibility that urine and feces might be mixed with each other within the bodily waste receiving space 31 is effectively alleviated because the separator 20a is substantially or really maintained in contact with the bodyside liner 2 at the bottom 6a of the crotch region 6. Consequentially, an anxiety that a liquidity of feces might be enhanced by admixture of urine and feces is effectively alleviated by the pants-type diaper 1. Even in the unlikely event that urine and/or feces is not guided into the bodily waste receiving space 31 but moves along the wearer's legs, the primary seals $51_R$, $51_L$ and the secondary seals $52_R$, $52_L$ provided around the wearer's legs cooperate together to prevent urine and/or feces from readily moving out beyond the leg-holes.

In the pants-type diaper 1 provided by the present invention, stock materials for the bodyside liner 2 may be selected from the group consisting of liquid-pervious nonwoven fabrics and perforated plastic films. Stock materials for the outside sheet 3 may be selected from the group consisting of liquid-impervious plastic films and laminated sheets composed of such plastic films and nonwoven fabrics. For the absorbent material 4, a mixture of fluff pulp and super-absorbent polymer particles, or fluff pulp alone, or a mixture of fluff pulp and super-absorbent polymer fibers may be used. For the wrapping sheet 4b, tissue paper often used may be replaced by appropriate nonwoven fabrics. As sheet materials for the separator 20, hydrophobic, or hydrophobic and liquid-impervious nonwoven fabrics or plastic films may be preferably used. More preferably, this sheet is elastically or inelastically extensible in response to elastic extension of the elastic members 21b, 22b. If the bodyside liner 2 and the outside sheet 3 and the other materials such as the separator 20 contain any heat-fusible plastics, these materials may be heat-sealed by means of sonic sealing technique.

The separator 20 of the basic structure 10a in FIG. 2 will be further discussed. The separator 20 is attached to the basic structure 10a so that a distance Hf from the transverse center line D-D to the front joint region 27 is equal to a distance Hr from the transverse center line D-D to the rear joint region 28. In the case of the separator 20 used by the pants-type diaper for baby, the distance Hf, Hr is preferably in a range of 20 to 150 mm, more preferably in a range of 40 to 80 mm. A dimension of the front joint region 27 and the rear joint region 28 measured in the transverse direction X in the preferred separator 20 is in a range of 3 to 50 mm, more preferably in a range of 10 to 30 mm. A dimension measured in the longitudinal direction Y is at least 3 mm.

The basic structure 10a of FIG. 2 further includes a pair of side flaps 25 defined by portions of the bodyside liner 2 and the outside sheet 3 extending outward in the transverse direction X beyond the transverse edges of the absorbent material 4. The side flaps 25 have a flexural stiffness in the transverse direction X lower than that of the absorbent material 4 and are correspondingly easier to be deformed. These side flaps 25 include the leg elastic portions 41. When the pants-type diaper 1 obtained from the basic structure 10a is in a state of FIG. 1 wherein the crotch region 6 curves in a U-shape, the side flaps 25 tend to raise themselves up along the lateral edges 4c of the absorbent material 4 under contraction of the elastic regions 41 in the vicinity of the transverse center line D-D, i.e., at the bottom 6a of the crotch region 6. On the other hand, the separator 20 is bonded along the lateral edges 23 thereof to the inner surface of the elastic regions 41 by means of adhesive 24. In response to deformation of the front and rear end edges 21, 22 of the separator 20 in a V-shape as shown in FIG. 4 from the state thereof shown in FIG. 2 wherein these front and rear end edges 21, 22 rectilinearly extend, these front and rear end edges 21, 22 function to pull the side flaps 25 toward the longitudinal center line C-C and thereby enhance the behavior of the side flaps 25 to raise themselves up. The side flaps 25 behaving in this manner are reliably held in close contact around the legs of the wearer from below and thereby effectively prevent leak of body fluids from possibly occurring around the legs.

Figure 5:
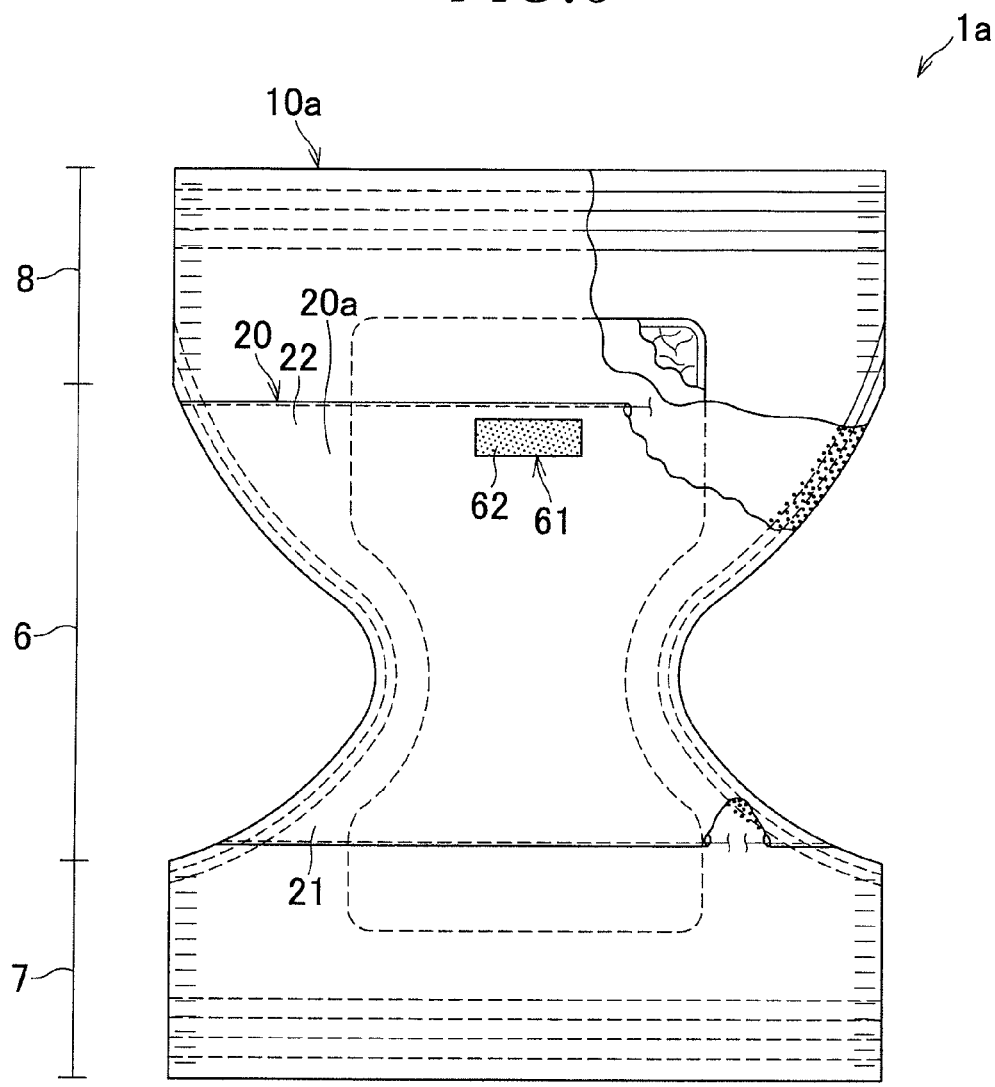
FIG. 5 is a view similar to FIG. 2, showing one preferred embodiment of the diaper as has been developed.
Figure 6:
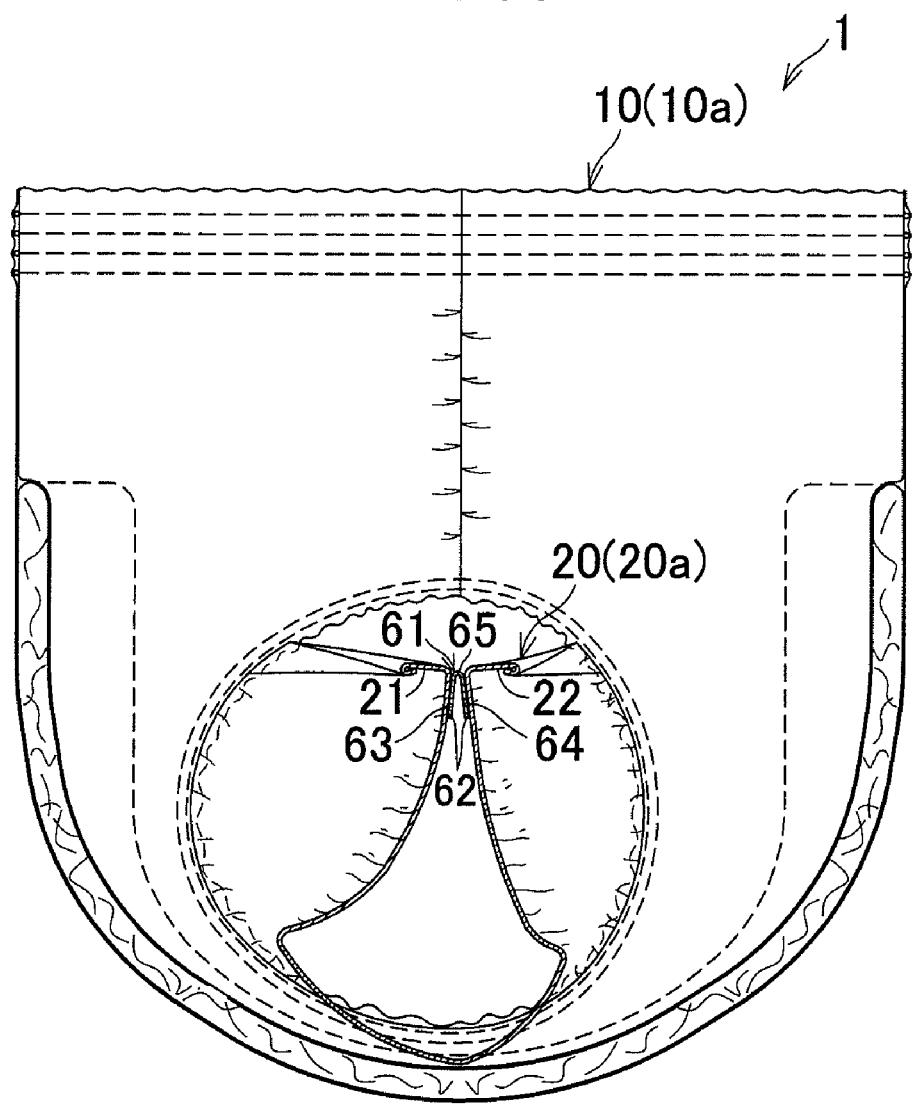
FIG. 6 is a view similar to FIG. 3, showing the diaper according to the embodiment as shown in FIG. 5.

FIGS. 5 and 6 are views respectively similar to FIGS. 2 and 3, showing one preferred embodiment of the developed diaper 1a used for the present invention and the pants-type diaper 1 obtained from this developed diaper 1a. In this developed diaper 1a, the rear end 22 of the separator 20 includes a joining member 61 attached thereto in order to integrate the rear end 22 with the front end 21. The joining member 61 is used as alternative means to formation of the joint region 35 by bonding the joint regions 27, 28 together by means of bonding agent in the case shown in FIG. 2. A manner in which this joining member 61 is used is illustrated in FIG. 6. As will be apparent from FIG. 6, the joining member 61 has an inverted V-shape cross-section and comprises a front section 63 adapted to be bonded to the front end 21 by means of bonding agent 62, a rear section 64 adapted to be bonded to the rear end 22 by means of bonding agent 62 and an intermediate section 65 extending between these front and rear sections 63, 64.

Figure 7:
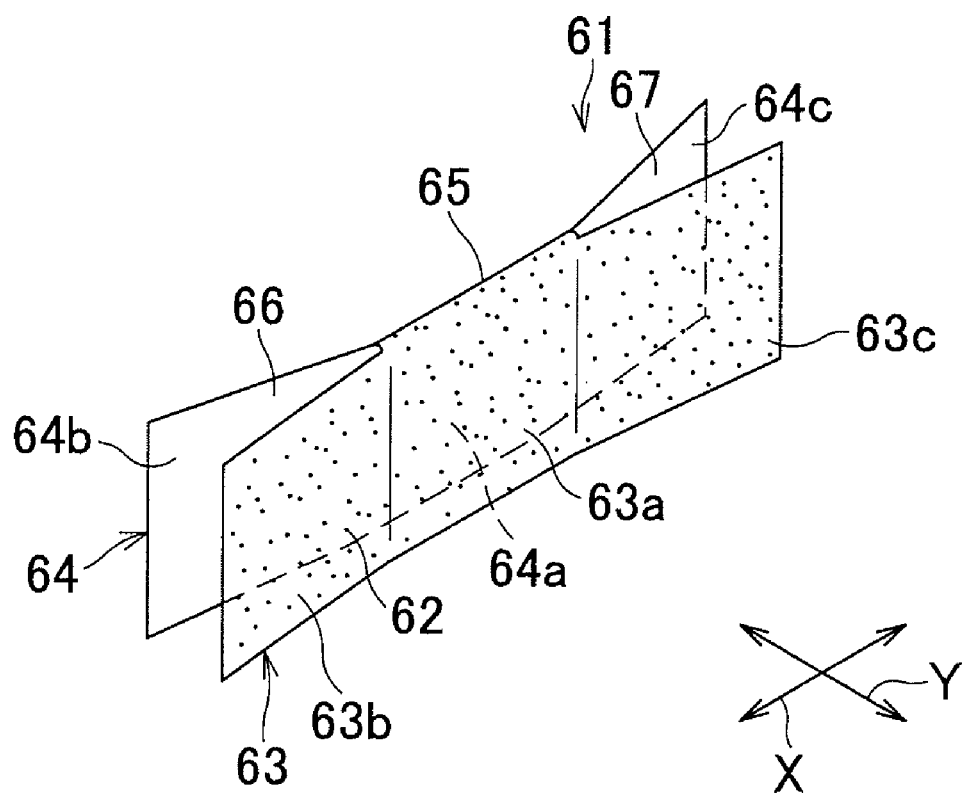
FIG. 7 is a perspective view of a joining member.

FIG. 7 is a perspective view showing the joining member 61. The joining member 61 is made of sheet materials such as nonwoven fabrics, woven fabrics, paper or plastic films and formed by folding back the sheet material along the intermediate section 65 wherein the front section 63 and the rear section 64 are coated on the outer surfaces thereof with bonding agent 62 such as hot melt adhesion or pressure-sensitive adhesive. While the front and rear sections 63, 64 are contiguous to each other at respective middle regions 63a, 64a of the joining member 61 as viewed in the transverse direction X, at respective end regions 63b, 63c; 64b, 64c thereof as viewed in the transverse direction X, these front and rear sections 63, 64 are separated from each other by the presence of slits 66, 67 formed in the joining member 61. Although the joining member 61 is not dimensionally specified, the respective end regions 63b, 63c; 64b, 64c may be dimensioned to be appropriately large to facilitate the operation that the front and rear end edges 21, 22 are bonded to each other by folding back the basic structure 10a in the developed diaper 1a of FIG. 5. In addition, it is unlikely that a free movement of the front and rear end edges 21, 22 might be encumbered by the presence of the joining member 61 even after these two ends 21, 22 have been integrated with each other using the joining member 61 unless the intermediate section 65 is dimensioned in the transverse direction X to be excessively large. When it is desired to dimension the intermediate section 65 of the joining member 61 to be relatively large in the back-and-forth direction Y, the slits 66, 67 may be dimensioned to be correspondingly large in the back-and-forth direction Y. In other words, the dimension of the intermediate section 65 in the back-and-forth direction Y may be adjusted to adjust the distance between the front and rear end edges 21, 22 of the separator 20a.

Figure 8:
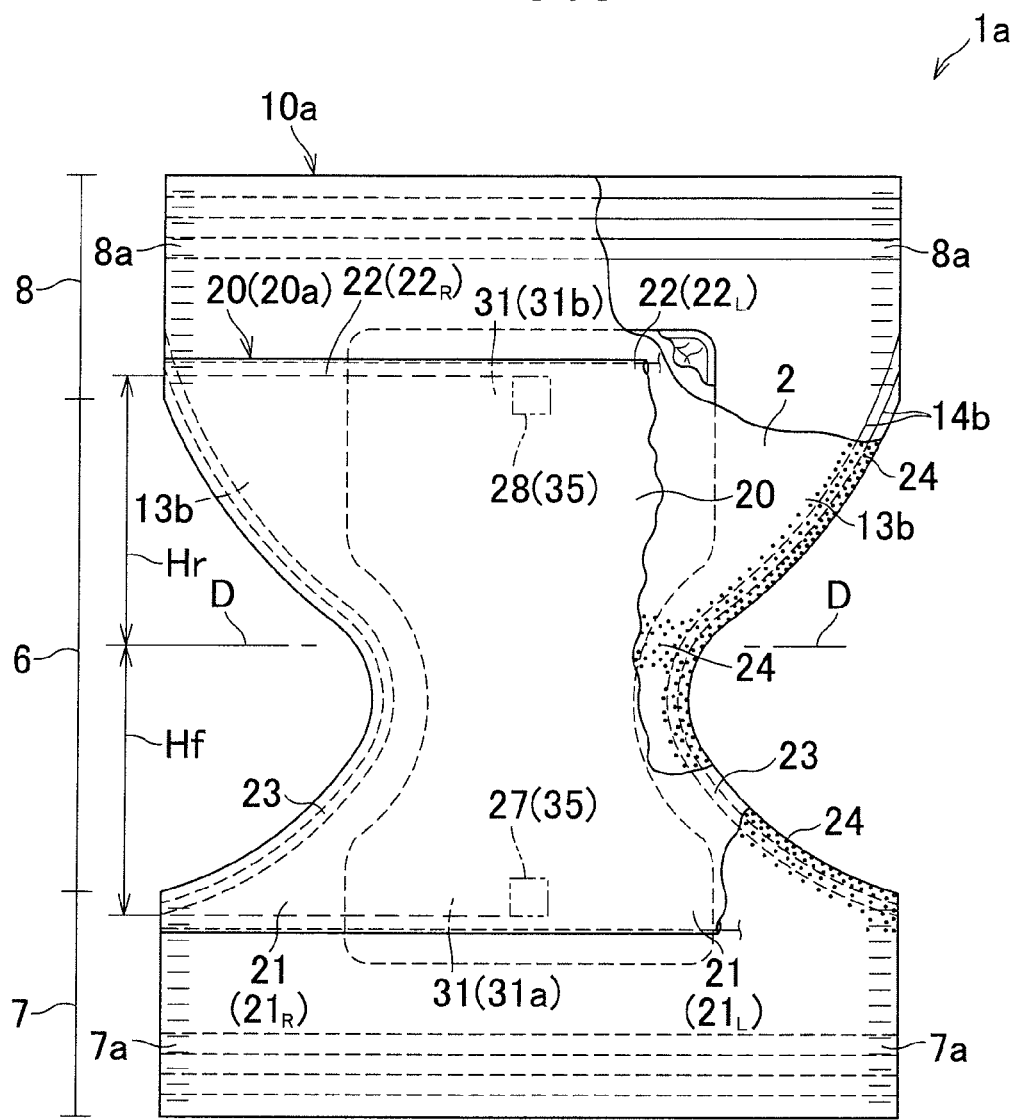
FIG. 8 is a view similar to FIG. 2, showing another preferred embodiment of the diaper as has been developed.

FIG. 8 is a view similar to FIG. 2, showing another preferred embodiment of the developed diaper 1a used for the present invention. Compared to the separator 20 in the basic structure 10a shown in FIG. 2, the basic structure 10a of FIG. 5 uses the separator 20 having a larger dimension in the back-and-forth direction Y. Of this separator 20, the front end 21 extends across the front waist region 7 between the transversely opposite margins 7a, 7a thereof. The rear end 22 extends across the rear waist region 8 between the transversely opposite margins 8a, 8a thereof. The transversely opposite margins 23 of this separator 20 are bonded to the basic structure 10a along the transversely opposite margins 7a, 7a thereof in the front waist region 7 as well as along the transversely opposite margins 8a, 8a thereof in the rear waist region 8. Then the front and rear joint regions 27, 28 may be bonded together to form the separator 20a. A zone in this separator 20a extending across the crotch region 6 along the transverse center line D-D, i.e., the zone extending between the transversely opposite margins is bonded to the topsheet 2 by means of hot melt adhesive 24 so that the bodily waste receiving space 31 defined by the separator 20a and the topsheet 2 is divided in two, i.e., a front receiving space 31a and a rear receiving space 31b. The basic structure 10a of FIG. 5 is folded back along the transverse center line D-D, then the transversely opposite margins 7a, 7a; 8a, 8a are bonded together and the joint region 27 associated with the front end 21 and the joint region 28 associated with the rear end 22 in the separator 20a are bonded together by means of hot melt adhesive or sonic sealing to form the joint region 35 (See FIG. 2) to obtain the pants-type diaper 1. In this pants-type diaper 1, the transversely opposite margins 13b including the leg elastic members 14b define the peripheries 13 of the respective leg-holes 12 as shown in FIGS. 1 and 3. These peripheries 13 are able to function as the secondary seals $52_R$, $52_L$ in FIG. 3. The front end 21 and the rear end 22 of the separator 20a lie at the equal distance Hf, Hr from the transverse center line D-D so that the transversely opposite margins 7a, 7a and 8a, 8a of the basic structure 10a may be bonded together, respectively, to obtain the front and rear end segments $21_R$, $22_R$ for the right leg and the front and rear end segments $21_L$, $22_L$ for the left leg. These front and rear end segments $21_R$, $22_R$; $21_L$, $22_L$ extending from the associated lateral margins $7a$, $8a$ to the joint region 35 of the front and rear end edges 21, 22. Now the wearer's right legs can be guided through a space defined between the front and rear end segments $21_R$, $22_R$ for the right leg and through a space defined between the front and rear end segments $21_L$, $22_L$ for the left leg, respectively. The front and rear end segments $21_R$, $22_R$ for the right leg function as the primary seal $51_R$ adapted to be held in close contact around the right leg while the front and rear end segments $21_L$, $22_L$ for the left leg function as the primary seal $51_L$ adapted to be held in close contact around the left leg. It should be noted here that the primary seals $51_R$, $51_L$ as well as the secondary seals $52_R$, $52_L$ to be formed from the basic structure $10a$ of FIG. 5 are distinguished from those shown in FIG. 4 in that these seals do not intersect with one another. Another important feature of the pants-type diaper 1 obtained from such basic structure $10a$ lies in that the separator $20a$ is bonded to the topsheet 2 in the vicinity of the transverse center line D-D by means of adhesive 24 and thereby a possibility that urine and feces might run into each other can be reliably prevented. An embodiment is also contemplated, in which the region of the separator $20a$ extending across the crotch region 6 and bonded to the topsheet 2 in the vicinity of the transverse center line D-D but aside forward from this center line D-D and not bonded to the topsheet 2 aside rearward from this center line D-D. Such arrangement inevitably results in reduced volume of the front receiving space $31a$ but does not affect the rear receiving space $31b$. According the present invention, the basic structure $10a$ and the separator $20a$ of FIG. 5 may be worked upon by following the same steps as for the developed diaper $1a$ of FIG. 2 to obtain the pants-type diaper 1 having the separator $20a$.

FIG. 9 is a view similar to FIG. 2, showing still another preferred embodiment of the developed diaper $1a$ used for the present invention. In the developed diaper $1a$ of FIG. 9, the separator 20 includes neither the front elastic members $21b$ nor the rear elastic members $22b$ as seen in FIG. 2. According to the embodiment shown by FIG. 9, the separator 20 itself is preferably made of elastic sheet materials such as elastically extensible and contractible nonwoven fabrics or plastic films but may be made of inelastic sheet materials. The separator $20a$ made of the elastic sheet material is substantially free from generation of gathers and it is unlikely in the case of such separator $20a$ that body fluids might flow between the wearer's skin and possibly generated gathers in uncontrollable direction. The separator $20a$ of FIG. 9 is provided with the joint regions 27, 28 each having a substantially rhombic shape which is relatively long in the back-and-forth direction Y. The front joint region 28 is coated with pressure-sensitive adhesives $28a$. The developed diaper $1a$ may be folded back along the transverse center line D-D to place the front and rear joint regions 27, 28 exactly upon each other and to bond them to each other. In this manner, the front and rear end edges 21, 22 of the separator 20 are integrated with each other. According to this embodiment of the invention also, the developed diaper $1a$ comprising this basic structure $10a$ and the separator 20 may be work upon in the same sequence as for the developed diaper $1a$ of FIG. 2 to obtain the pants-type diaper 1 including the separator $20a$.

Figure 10:
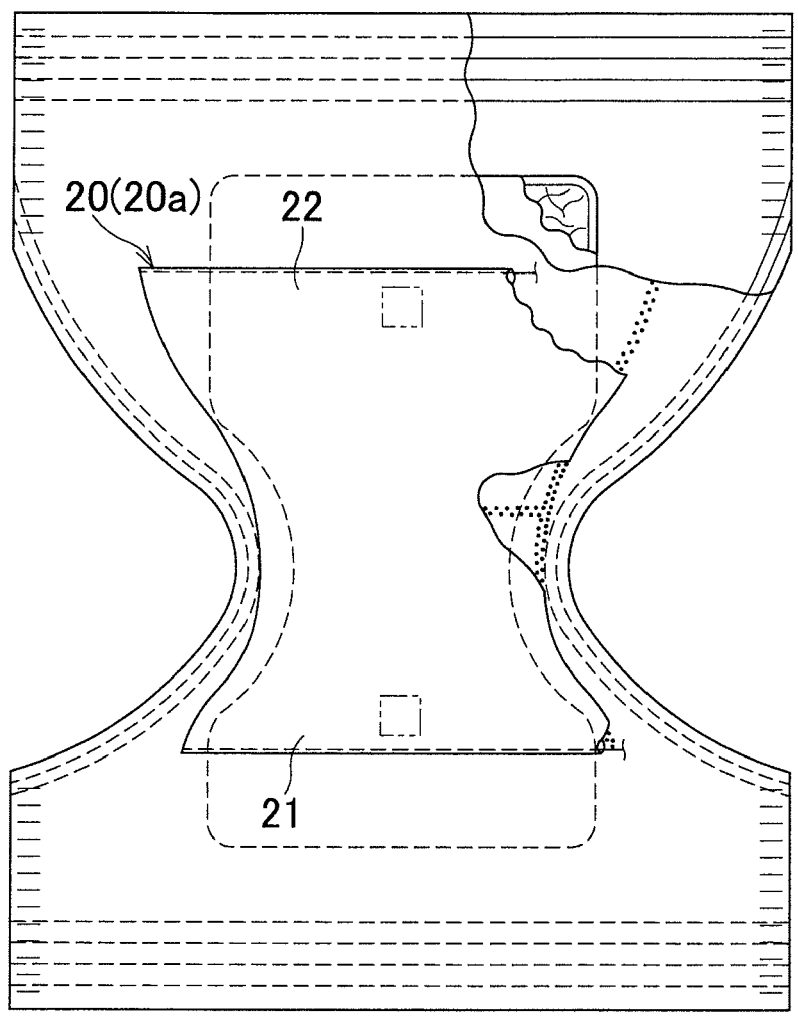
FIG. 10 is a view similar to FIG. 2, showing yet another preferred embodiment of the diaper as has been developed.

FIG. 10 is a view similar to FIG. 2, showing yet another preferred embodiment of the developed diaper $1a$ used for the present invention. The separator 20 in the basic structure $10a$ of FIG. 10 has its dimension in the transverse direction X which is shorter than that of the separator 20 in FIG. 2. When it is not desired to hold the front and rear end edges 21, 22 of the separator $20a$ in close contact around the legs over a wide range, even such separator 20 having a relatively small dimension in the transverse direction X is useful. According to this embodiment also, the developed diaper $1a$ comprising this basic structure $10a$ and the separator 20 may be work upon in the same sequence as for the developed diaper $1a$ of FIG. 2 to obtain the pants-type diaper 1.

Figure 11:
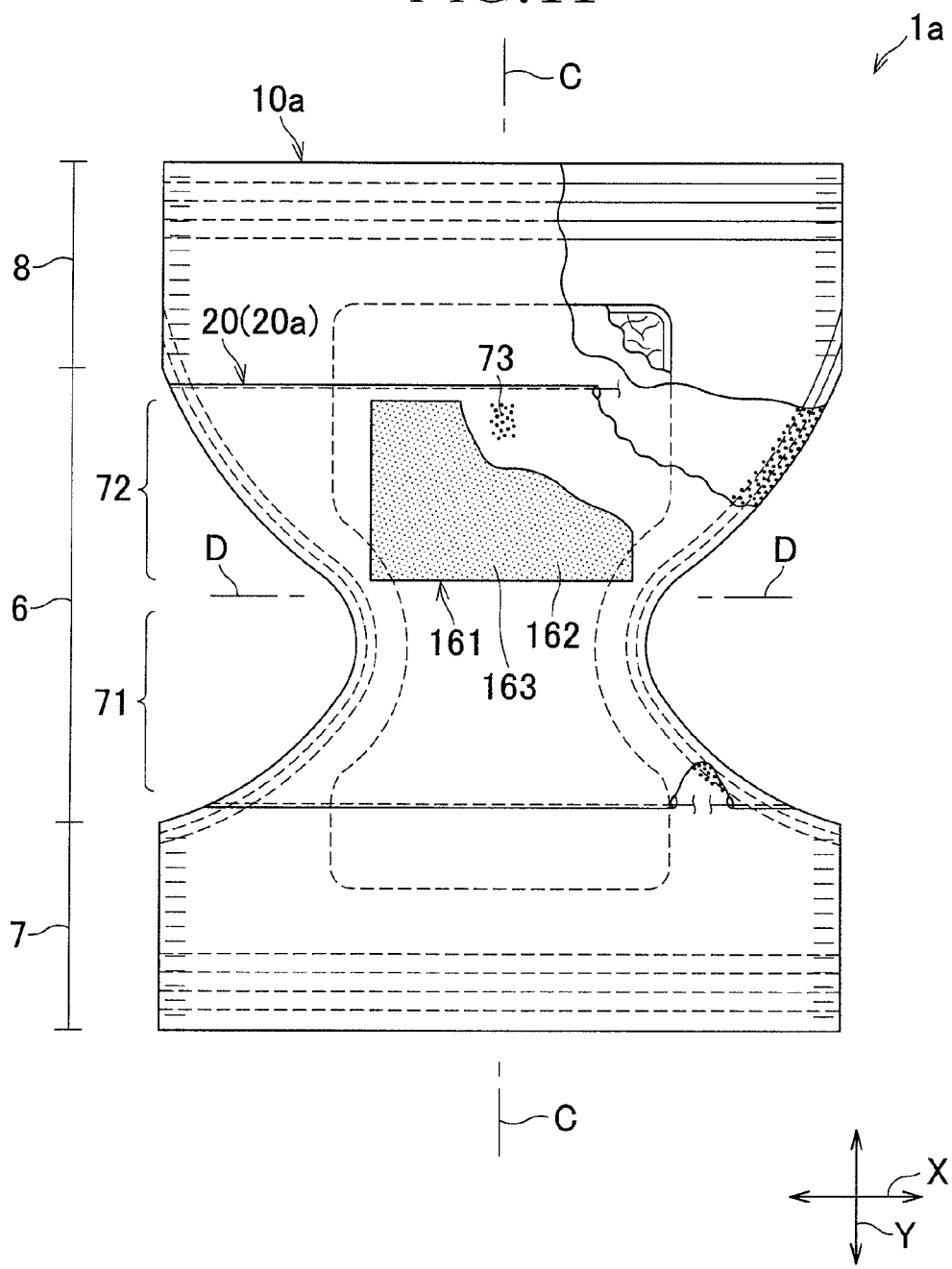
FIG. 11 is a view similar to FIG. 5, showing further another preferred embodiment of the diaper as has been developed.
Figure 12:
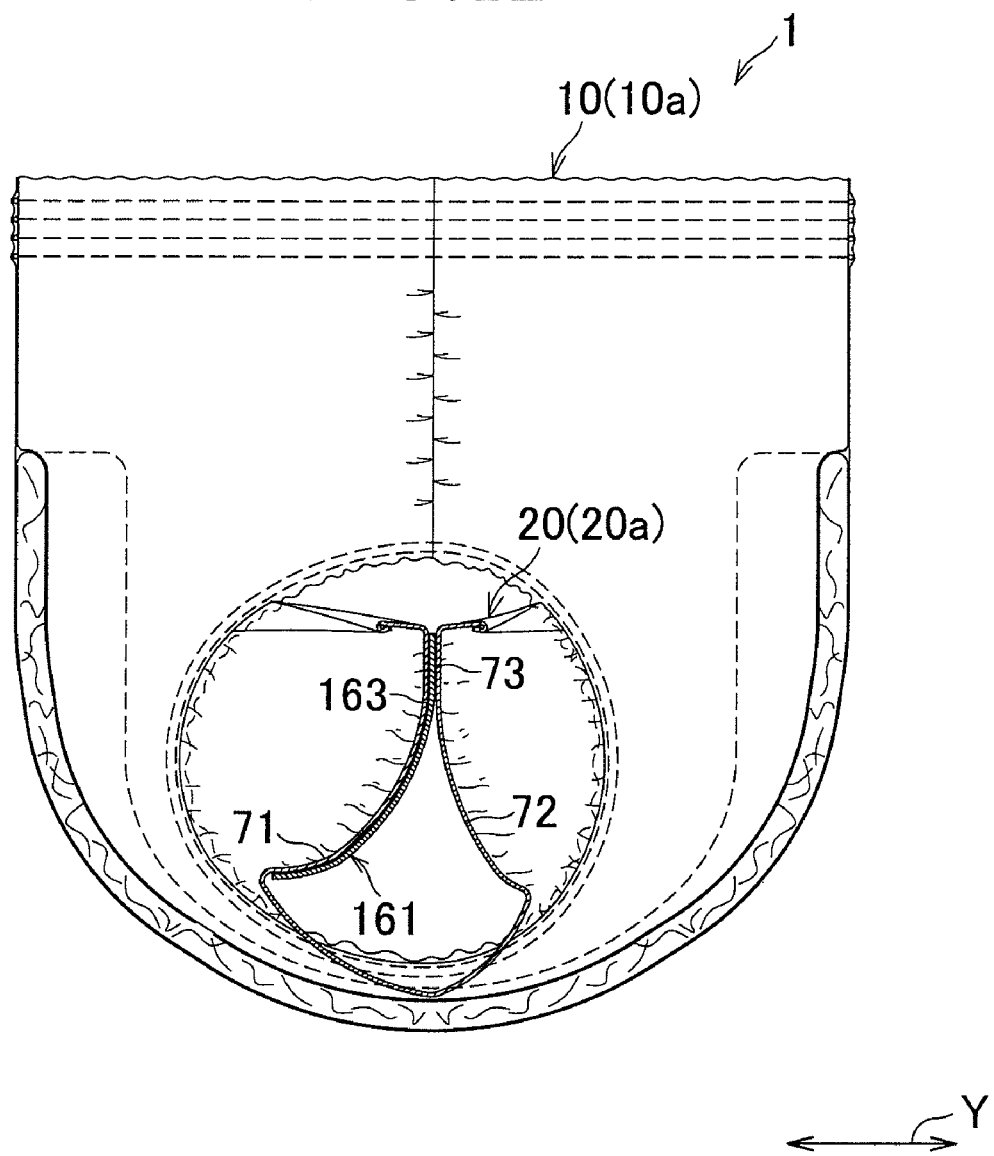
FIG. 12 is a view similar to FIG. 6, showing the pants-type diaper obtained from the developed diaper as shown in FIG. 11.

FIGS. 11 and 12 are views similar to FIGS. 5 and 6, respectively, illustrating further another preferred developed diaper $1a$ used for the present invention. In the developed diaper $1a$ of FIG. 11, the joining member 61 of FIG. 5 is replaced by a joining member 161. The basic structure $10a$ is provided with the separator 20 attached thereto. This separator 20 comprises a first half 71 extending so as to be put aside from the transverse center line D-D toward the front waist region 7 and a second half 72 extending so as to be put aside from the transverse center line D-D toward the rear waist region 8. The joining member 161 is formed of a separator which is symmetric about the longitudinal center line C-C and permanently bonded to the inner surface of the second half 72 by means of adhesive 73. The adhesive 73 is present on the second half 72 only in the vicinity of the longitudinal center line C-C. On both sides of the adhesive 73 in the transverse direction X, i.e., on both sides of the longitudinal center line C-C, the second half 72 and the joining member 161 are not bonded to each other and spaced from each other. The joining member 161 is coated on its inner surface 162 with adhesive 163. Such developed diaper $1a$ is folded back along the transverse center line D-D with the separator 20 inside, then the first half 71 of the separator 20 is permanently bonded to the joining member 161 by means of the adhesive 163 and the transversely opposite margins $7a$, $8a$ of the front and rear waist regions 7, 8 of the basic structure $10a$ are put flat and bonded together to obtain the pants-type diaper 1. As will be apparent from FIG. 12, the joining member 161 is bonded to the second half 72 of the separator 20 by means of the adhesive 73 and bonded to the first half 71 by means of the adhesive 163 so that the separator 20 forms the separator $20a$ just as the separator 20 of FIG. 6 forms the separator $20a$.

In the developed diaper $1a$ of FIG. 11, the separator 20 may be fixed to the basic structure $10a$ after the joining member 161 has been attached to the separator 20 or the joining member 161 may be attached to the separator 20 after the separator 20 has been fixed to the basic structure $10a$. The joining member 161 may be previously coated with the adhesive 163 or the joining member 161 may be coated with the adhesive 163 after the joining member 161 has been attached to the second half 72. The joining member 161 on the developed diaper $1a$ is dimensioned to be smaller than both the first half 71 and the second half 72. However, in the case of the crotch region 6 configured symmetrically about the transverse center line D-D in the basic structure $10a$, it is possible to match the dimension of the joining member 161 to the dimension of the basic structure $10a$ and to bond this joining member 161 to the transversely opposite margins $13b$ of the crotch region. The joining member 161 may be formed using the sheet material similar to that for the joining member 61.

In the pants-type diaper 1 comprising the first half 71 and the second half 72 bonded by means of the joining member 161 as in the illustrated embodiment, the joining member 161 may be dimensioned to be sufficiently large to ensure that these first and second halves 71, 72 can be easily bonded to each other without exact control for putting the first half 71 and the second half 72 flat together. In the case of the pants-type diaper 1 of FIG. 12, the joining member 161 is bonded to the first half 71 over a relatively large area while the joining member 161 is bonded to the second half 72 over a relatively small area so that bonding areas to the first and second halves may be reduced regardless of using the relatively large joining member 161.

While the method for making the disposable pants-type diaper 1 according to the present invention has been described hereinbefore with respect to several particular embodiments in which the method starts from the individual basic structure 10a and the individual separator 20 attached thereto, the present invention is not limited to these particular embodiments. Without departing from the spirit and the scope of the invention, to obtain a series of the pants-type diapers 1 which are contiguous one to another in a web-like manner from a plurality of the basic structures 10a which are contiguous one to another in the transverse direction X or in the back-and-forth direction Y and a plurality of the separators 20 which are contiguous one to another in the transverse direction X or in the back-and-forth direction Y. In the latter case, the web-like series of the pants-type diapers 1 which are contiguous one to another may be cut into the individual pants-type diapers 1 in the final step.

The present invention makes it possible to obtain the disposable pants-like diaper facilitating the bodily waste receiving space of the diaper to be exactly opposed to the wearer's anus and protecting the wearer's skin from being contaminated with urine and/or feces.

What is claimed is:

1. A method for making a disposable pants-type diaper comprising:
    the steps of preparing a basic structure having a crotch region, a front waist region extending forward from said crotch region and a rear waist region extending rearward from said crotch region, bonding said front and rear waist regions to each other along transversely opposite margins of said front and rear waist regions to make said basic structure in a pants-shape and providing said basic structure on its inner side facing the wearer's skin with s separator adapted to prevent feces from coming in contact with the wearer' skin, said method for making the disposable pants-type diaper further comprising the steps of:
    preparing a separator extending on said inner side of said basic structure in a back-and-forth direction of said crotch region from a longitudinal middle of said crotch region into said front and rear waist regions, and extending in a transverse direction of said crotch region so as to straddle a longitudinal center line bisecting a transverse dimension of said crotch region;
    fixing transversely opposite margins of said separator extending in said back-and-forth direction to said inner side on both sides of said longitudinal center line, and spacing a region of said separator defined between said transversely opposite margins;
    folding back said basic structure in said back-and-forth direction along a transverse center line with said separator inside and then integrating a front end of said separator extending in parallel to said transverse center line with a rear end of said separator extending in parallel to said transverse center line on said longitudinal center line; and
    bonding transversely opposite margins of said front waist region to the transversely opposite margins of said rear waist region in said basic structure to form said separator from said separator.

2. The method according to claim 1, wherein said front and rear end edges of said separator are integrated with each other in a joining region previously formed by bonding agent such as hot melt adhesive or pressure-sensitive adhesive.

3. The method according to claim 2, wherein said joining region is formed by folding back a sheet-like joining member coated on its one surface with said bonding agent along a folding line extending in parallel to said transverse center line with said bonding agent outside and then bonding one of halves formed as a result of folding back to associated one of said front and rear end edges.

4. The method according to claim 1, wherein said front and rear end edges of said separator are integrated with each other by means of sonic or heat sealing technique.

5. The method according to claim 1, further including a step of partially bonding the region of said separator defined between said transversely opposite margins to said basic structure in a vicinity of said transverse center line.

6. A method for making a disposable pants-type diaper basically comprising the steps of preparing a basic structure having a crotch region, a front waist region extending forward from said crotch region and a rear waist region extending rearward from said crotch region, bonding said front and rear waist regions to each other along transversely opposite margins of said front and rear waist regions to make said basic structure in a pants-shape and providing said basic structure on its inner side facing the wearer's skin with a separator adapted to prevent feces from coming in contact with the wearer' skin, said method for making the disposable pants-type diaper further comprising the steps of:
    preparing a first separator comprising a first half extending on said inner side of said basic structure so as to be put aside toward said front waist region from a transverse center line bisecting a dimension of said basic structure and a second half extending on said inner side of said basic structure so as to be put aside toward said rear waist region from said transverse center line, said first separator extending in said transverse direction of said crotch region so as to stride a longitudinal direction bisecting a transverse dimension of said crotch region;
    fixing transversely opposite margins of said first separator extending in said back-and-forth direction to said inner side on both sides of said longitudinal center line, and spacing a region of said first separator defined between said transversely opposite margins;
    placing a second separator not larger than one of the first and second halves upon said one of the first and second halves;
    bonding said one of the halves and said second separator to each other on said longitudinal center line while said one of the halves is left spaced from said second separator on both sides of said longitudinal center line;
    coating the second separator on its surface opposite to its surface bonded to said one of the halves with adhesive;
    folding back said basic structure along said transverse center line in said back-and-forth direction with said first separator inside;
    bonding the other of the halves to said opposite surface of said second separator by means of said adhesive; and
    bonding transversely opposite margins of said front waist region to the transversely opposite margins of said rear waist region in said basic structure to form said separator from said first separator.

7. The method according to claim 6, wherein said first separator is fixed to the inner side of said basic structure after said second separator has previously been bonded to said one of the halves.

* * * * *